United States Patent
Han et al.

(10) Patent No.: US 11,298,346 B2
(45) Date of Patent: Apr. 12, 2022

(54) METHODS FOR TREATMENT OF FIBROTIC DISEASES

(71) Applicant: Beta Cat Pharmaceuticals, Inc., Houston, TX (US)

(72) Inventors: Ruolan Han, Houston, TX (US); Jon Northrup, Houston, TX (US); Srinivas Kasibhatla, Houston, TX (US); Stephen Horrigan, Houston, TX (US); Jeffrey Larson, Houston, TX (US)

(*) Notice: Subject to any disclaimer, the term of this patent is extended or adjusted under 35 U.S.C. 154(b) by 0 days.

(21) Appl. No.: 15/995,917

(22) Filed: Jun. 1, 2018

(65) Prior Publication Data
US 2018/0344713 A1 Dec. 6, 2018

Related U.S. Application Data (60) Provisional application No. 62/514,541, filed on Jun. 2, 2017.

(51) Int. Cl.
*A61K 31/445* (2006.01)
*A61P 11/00* (2006.01)
(Continued)

(52) U.S. Cl.
CPC .......... *A61K 31/445* (2013.01); *A61K 9/0078* (2013.01); *A61K 9/10* (2013.01);
(Continued)

(58) Field of Classification Search
CPC .................................................. A61K 31/445
(Continued)

(56) References Cited

U.S. PATENT DOCUMENTS 8,129,519 B2\* 3/2012 Cholody ............... C07C 311/20
540/1
2013/0143920 A1 6/2013 Bhalla
(Continued)

FOREIGN PATENT DOCUMENTS

WO 2010059142 A1 5/2010

OTHER PUBLICATIONS

Guo et al, Physiol Res (2012), vol. 61, pp. 337-346. (Year: 2012).\*
(Continued)

*Primary Examiner* — Craig D Ricci
*Assistant Examiner* — Janet L Coppins
(74) *Attorney, Agent, or Firm* — Wood, Phillips, Katz, Clark & Mortimer

(57) ABSTRACT

Methods for treatment of fibrotic diseases using compounds of formula I

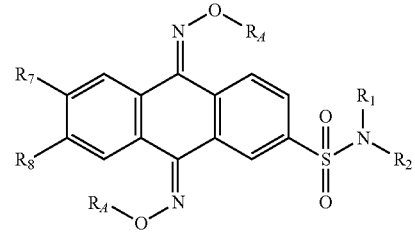

Formula I wherein $R_A$ is hydrogen,
$R_7$ and $R_8$ are independently selected from H and $SO_2NR_3R_4$,
one of $R_7$ and $R_8$ is hydrogen, and
$R_1$, $R_2$, $R_3$, and $R_4$ are each independently selected from H, alkyl, heteroalkyl, cycloalkyl, arylcycloalkyl, aryl,
(Continued)

heteroaryl, heterocycloalkyl, and each of $NR_1R_2$ and $NR_3R_4$ can independently combine to form a heterocycloalkyl, and wherein said alkyl, heteroalkyl, cycloalkyl, arylcycloalkyl, aryl, heteroaryl, or heterocycloalkyl may be optionally substituted, or a pharmaceutically acceptable salt, ester, amide, stereoisomer, geometric isomer or prodrug thereof.

6 Claims, 6 Drawing Sheets

(51) Int. Cl.
*A61K 9/10* (2006.01)
*A61K 47/10* (2017.01)
*A61K 9/00* (2006.01)
*A61P 19/00* (2006.01)
*A61P 17/02* (2006.01)

(52) U.S. Cl.
CPC ............. *A61K 47/10* (2013.01); *A61P 11/00* (2018.01); *A61P 17/02* (2018.01); *A61P 19/00* (2018.01); *A61K 9/0014* (2013.01); *A61K 9/0021* (2013.01); *A61K 9/0043* (2013.01); *A61K 9/0073* (2013.01)

(58) Field of Classification Search
USPC .......................................................... 514/316
See application file for complete search history.

(56) References Cited

U.S. PATENT DOCUMENTS

2015/0313873 A1 11/2015 Cholody et al.
2017/0029450 A1 2/2017 Vankayalapat et al.

OTHER PUBLICATIONS

Henderson et al, PNAS (2010), vol. 107(32), pp. 14309-14314. (Year: 2010).*
International Search Report for corresponding PCT application No. PCT/US2018/035646 dated Aug. 31, 2018.
Huang et al.'Fibroproliferative Disorders and Their Mechanobiology', Connective Tissue Research, Feb. 13, 2012 (Feb. 13, 2012), vol. 53, pp. 187-196; Abstract.

* cited by examiner

METHODS FOR TREATMENT OF FIBROTIC DISEASES

FIELD OF THE INVENTION

The present invention relates to the field of treatment of fibrotic diseases, including pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis, desmoid tumors and other conditions.

BACKGROUND OF THE INVENTION

Fibrotic diseases, including pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis, and desmoid tumors are important conditions which often cause morbidity and mortality and can affect all tissues and organ systems.

Pulmonary fibrosis is a condition in which the lung tissue becomes thickened, stiff, and scarred. While the cause of the fibrosis (scarring) can be sometimes determined, often the etiology of this condition remains unknown. When there is no known cause for the development of pulmonary fibrosis (and certain radiographic and/or pathologic criteria for pulmonary fibrosis are met), the disease is called idiopathic pulmonary fibrosis (IPF).

IPF has no specific demographic profile, and may be found in both urban and rural environments. Risk factors of IPF include smoking and certain genetic factors. IPF affects more men than women and usually occurs between the ages of 50 and 70.

Dupuytren's contracture, which is alternatively known as palmar fibromatosis (or "Dupuytren's disease"), is a disease associated with the build-up of extracellular matrix materials such as collagen on the connective tissue of the hand (the palmar fascia), causing it to thicken and shorten with the physical effect of causing the fingers to curl, most commonly the ring finger and little finger. Dupuytren's contracture is manifested through progressive flexion contracture of the digits of the hand, resulting in significantly compromised function. It affects both males and females, but the incidence is higher in males.

The causes of Dupuytren's disease are not well understood and underlying disease is not currently curable.

Accordingly, there is a need for novel methods of treating fibrotic diseases.

SUMMARY OF THE INVENTION

The present invention is directed to the observation the WNT/beta catenin signaling is an important mediator of fibrotic diseases and that inhibition of this signaling pathway ameliorates fibrosis and fibrotic disease states. Inhibitors of the Wnt/beta-catenin signaling pathway can be used for the treatment and/or prevention of fibrotic diseases, including but not limited to pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis, and desmoid tumors.

The invention includes all possible methods of administration, including intravenous, parenteral, oral, inhalation (including aerosolized delivery), buccal, intranasal, rectal, intra-lesional, intraperitoneal, intradermal, transdermal, subcutaneous, intra-arterial, intracardiac, intraventricular, intracranial, intratracheal, intrathecal administration, intramuscular injection, intravitreous injection, and topical application.

In one embodiment, the invention is directed to aerosolized delivery of such compounds, in particular for treating pulmonary conditions. In another embodiment, the invention provides intravenous injection for treating Dupuytren's contracture. In yet another embodiment, the invention provides topical application for treatment of keloids.

Accordingly, the present invention provides methods for treating and/or preventing fibrotic diseases comprising administering to a patient in need thereof a therapeutically effective amount of a compound of formula I Formula I wherein $R_4$ is hydrogen, $R_7$ and $R_8$ are independently selected from H and $SO_2NR_3R_4$, one of $R_7$ and $R_8$ is hydrogen, and

$R_1$, $R_2$, $R_3$, and $R_4$ are each independently selected from H, alkyl, heteroalkyl, cycloalkyl, arylcycloalkyl, aryl, heteroaryl, heterocycloalkyl, and each of $NR_1R_2$ and $NR_3R_4$ can independently combine to form a heterocycloalkyl, and wherein said alkyl, heteroalkyl, cycloalkyl, arylcycloalkyl, aryl, heteroaryl, or heterocycloalkyl may be optionally substituted, or a pharmaceutically acceptable salt, ester, amide, stereoisomer, geometric isomer or prodrug thereof.

U.S. Pat. No. 8,129,519 describes methods of making the compounds of the invention. In one embodiment, the invention contemplates the use of any of the compounds of the U.S. Pat. No. 8,129,519 for treating and/or preventing fibrotic diseases according to the present invention.

In one preferred embodiment, $NR_1R_2$ and $NR_3R_4$ are independently 6- to 15-membered heterocycloalkyl containing one nitrogen in the ring.

In a preferred embodiment, the compound of formula I has the following structure:

or a pharmaceutically acceptable salt, ester, amide, stereoisomer, geometric isomer or prodrug thereof. This compound is also known as BC-2059 or Tegavivint. U.S. Pat. No. 8,129,519 describes methods of making this compound.

In one embodiment, the fibrotic disease is selected from the group consisting of pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis.

In a preferred embodiment, the disorder is pulmonary fibrosis.

In another preferred embodiment, the disorder is Dupuytren's contracture.

In yet another preferred embodiment, the disorder is keloids.

In one embodiment, the invention provides a method of treating pulmonary fibrosis comprising a systemic administration or an aerosolized delivery of Tegavivint to a patient in need thereof.

DETAILED DESCRIPTION OF THE INVENTION

Definitions

The following definitions are used, unless otherwise described.

The term "subject" includes mammals, including humans. The terms "patient" and "subject" are used interchangeably.

The term "therapeutically effective amount" means the amount of a compound that, when administered to a subject for treating a disease or disorder, is sufficient to affect the disease or disorder. The "therapeutically effective amount" can vary depending on the variety of factors, including the compound, the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

In one embodiment, the terms "treating" or "treatment" refer to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq.

Pharmaceutically acceptable salts include, but are not limited to, acid addition salts. For example, the nitrogen atoms may form salts with acids. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid and citric acid.

Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Compounds useful for the purposes of the invention can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds useful for the purposes of the invention may comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively.

Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds useful for the purposes of the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

For example, a "C1-C3 alkyl" group can be selected from methyl, ethyl, n-propyl, i-propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted. As a further example, a "C1-C12 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, nitrile, sulfonamide, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "halogen," "halide," and "halo," as used herein, refer to the halogens fluorine, chlorine, bromine, and iodine. It is also contemplated that, in various aspects, halogen can be selected from fluoro, chloro, bromo, and iodo. For example, halogen can be selected from fluoro, chloro, and bromo. As a further example, halogen can be selected from fluoro and chloro. As a further example, halogen can be selected from chloro and bromo. As a further example, halogen can be selected from bromo and iodo. As a further example, halogen can be selected from chloro, bromo, and iodo. In one aspect, halogen can be fluoro. In a further aspect, halogen can be chloro. In a still further aspect, halogen is bromo. In a yet further aspect, halogen is iodo.

It is also contemplated that, in certain aspects, pseudohalogens (e.g. triflate, mesylate, tosylate, brosylate, etc.) can be used in place of halogens. For example, in certain aspects, halogen can be replaced by pseudohalogen. As a further example, pseudohalogen can be selected from triflate, mesylate, tosylate, and brosylate. In one aspect, pseudohalogen is triflate. In a further aspect, pseudohalogen is mesylate. In a further aspect, pseudohalogen is tosylate. In a further aspect, pseudohalogen is brosylate.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds suitable for the purposes of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Unless the present specification uses a different definition, all of the definitions and other disclosures of U.S. Pat. No. 8,129,519 are expressly incorporated herein by reference.

DETAILED DESCRIPTION OF THE INVENTION

The present invention is directed to the observation the WNT/beta catenin signaling is an important mediator of fibrotic diseases and that inhibition of this signaling pathway ameliorates fibrosis and fibrotic disease states. Inhibitors of the Wnt/beta-catenin signaling pathway can be used for the treatment and/or prevention of fibrotic diseases, including but not limited to pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis, and desmoid tumors.

Accordingly, the present invention provides methods for treating and/or preventing fibrotic diseases comprising administering to a patient in need thereof a therapeutically effective amount of a compound of formula I Formula I wherein $R_A$ is hydrogen,
$R_7$ and $R_8$ are independently selected from H and $SO_2NR_3R_4$, one of $R_7$ and $R_8$ is hydrogen, and

$R_1$, $R_2$, $R_3$, and $R_4$ are each independently selected from H, alkyl, heteroalkyl, cycloalkyl, arylcycloalkyl, aryl, heteroaryl, heterocycloalkyl, and each of $NR_1R_2$ and $NR_3R_4$ can independently combine to form a heterocycloalkyl, and wherein said alkyl, heteroalkyl, cycloalkyl, arylcycloalkyl, aryl, heteroaryl, or heterocycloalkyl may be optionally substituted, or a pharmaceutically acceptable salt, ester, amide, stereoisomer, geometric isomer or prodrug thereof.

In one preferred embodiment, $NR_1R_2$ and $NR_3R_4$ are independently 6- to 15-membered heterocycloalkyl containing one nitrogen in the ring.

U.S. Pat. No. 8,129,519 describes methods of making the compounds of the invention.

In a preferred embodiment, the compound of formula I has the following structure:

or a pharmaceutically acceptable salt, ester, amide, stereoisomer or geometric isomer thereof. The compound is also known as BC-2059 or Tegavivint. U.S. Pat. No. 8,129,519 describes methods of making this compound.

In one embodiment, the fibrotic disease is selected from the group consisting of pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis.

In a preferred embodiment, the disorder is pulmonary fibrosis.

In another preferred embodiment, the disorder is Dupuytren's contracture.

In yet another preferred embodiment, the disorder is keloids.

BC-2059 was originally identified in a cell based screen for its ability to inhibit the transcriptional activation of the WNT/beta catenin signaling pathway. Characterization of this compound series led to the discovery that members of this compound series were able to induce the degradation of beta-catenin, interfere with the beta catenin transcriptional activation complex, and had characteristics of a nuclear receptor signaling pathway modulator. BC-2059 was found to interact with TBL1 and prevent beta-catenin from associating with TBL1 and leads to beta-catenin degradation.

This activity of BC-2059 was found to inhibit the beta catenin pathway in cancer cells and cause those cells to undergo apoptosis. Specifically, cell lines derived from chromic myeloid leukemia (CML) patients and cell lines and primary cells derived from myeloproliferative neoplasm (MPN) patients undergo apoptosis and growth inhibition in the presence of BC-2059. In addition, the activity of BC-2059 is synergistic with compounds that affect therapeutically important signaling pathways in these diseases (such as Janus kinase 2 (JAK2), break point cluster-Abelson (BCR-ABL), and Histone deacetylase (HDACs) inhibitors and can be used in combination with these agents to ameliorate these diseases in individuals with the disease.

Thus, in some embodiments, the provided agents can be used in combination with other therapeutic agents, including but not limited to tyrosine kinase inhibitor (including but not limited to nilotinib), histone deacetylase inhibitor (including, but not limited to panobinostat), other anti-cancer agents and other therapeutic agents.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients.

The total daily dose of the compounds of this invention administered to a human or lower animal may range from about 0.0001 to about 1000 mg/kg/day. If desired, the effective daily dose can be divided into multiple doses for purposes of administration; consequently, single dose compositions may contain such amounts or submultiples thereof to make up the daily dose.

For a clearer understanding of the invention, details are provided below. These are merely illustrations and are not to be understood as limiting the scope of the invention in any way. Indeed, various modifications of the invention in addition to those shown and described herein will become apparent to those skilled in the art from the following examples and foregoing description. Such modifications are also intended to fall within the scope of the appended claims.

EXAMPLES

Example 1

Effects of Tegavivint on Primary Cell Models of Fibrotic (Dupuytren's Disease) and Non-Fibrotic Palmar Fascia Experimental Conditions Tegavivint (BC-2059) powder was reconstituted it in 100% dimethyl sulfoxide (DMSO) to a 10_mM stock solution. The stock was diluted to 100 nM in serum-free media ($\alpha$ minimal essential medium, $\alpha$MEM), and further diluted to 100 pM in serum-free $\alpha$MEM immediately before the analyses were performed. Serial dilutions from 100 pM down to 0.78 pM were assessed in various assays. 0.001% DMSO in $\alpha$MEM was used as the vehicle control, and $\alpha$MEM alone was used as an untreated control, in a subset of analyses.

Proliferation/viability analyses were performed in triplicate on primary palmar fascia fibroblasts derived from the fibrotic palmar fascia (DD cells) of 2 patients with Dupuytren's disease (DD249, DD77) and syngeneic primary palmar fascia fibroblasts derived from visibly non-fibrotic palmar fascia (PF cells) from these patients (PF249, PF77). Cells were cultured on type-1 collagen coated 96 well trays for these analyses to better replicate substrate interactions in vivo. Two independent assays were used for these analyses: Alamar Blue assays for analyses up to 72 hrs in cells derive from 1 patient, and Water Soluble Tetrazolium-(WST-1) assays for analyses up to 24 hrs in cells derived from the other patients. Significant effects of treatment on proliferation over time were detected by ANOVA repeated measures.

Gene expression analyses were assessed in triplicate on a Real-Time PCR ABI Prism 7500. Total RNA samples were derived from syngeneic DD and PF cells cultured from the explant tissues from one patient with Dupuytren's disease (DD180 and PF 180) and 1 patient with no history of Dupuytren's disease (CT38) as a normal allogeneic control. RNA quality was assessed on an Agilent 2100 Bioanalyzer and 2 μg of high quality total RNA was reverse transcribed into cDNA first strand using the High-Capacity cDNA Archive Kit (Applied Biosystems) in accordance with the manufacturer's instructions. TaqMan gene expression assays were used to measure CTNNB1, EGR1, NRG1 and WISP1 mRNA levels after 48 hrs of treatment in cells cultured on type-1 collagen coated 6 well trays. The ΔΔCT method was used after confirmation of parallel PCR amplification efficiencies of target and housekeeping genes PCR reactions were carried out under the following conditions: Initial denaturation at 95° C. for 5 min followed by cycles of denaturation (95° C. for 15 sec), primer annealing (60° C. for 1 min) and transcript extension (50° C. for 2 min) for 40 cycles.

Fibroblast populated collagen lattice assays were performed on primary palmar fascia fibroblasts derived from the fibrotic palmar fascia of one patient with Dupuytren's disease (DD180) using the protocol described in Raykha, C., Crawford, J., Gan, B. S., Fu, P., Bach, L. A., and O'Gorman, D. B. (2013) IGF-II and IGFBP-6 regulate cellular contractility and proliferation in Dupuytren's disease. *Biochimica et biophysica acta*. 1832, 1511-9.

Experimental Results

Figures 1A, 1B:
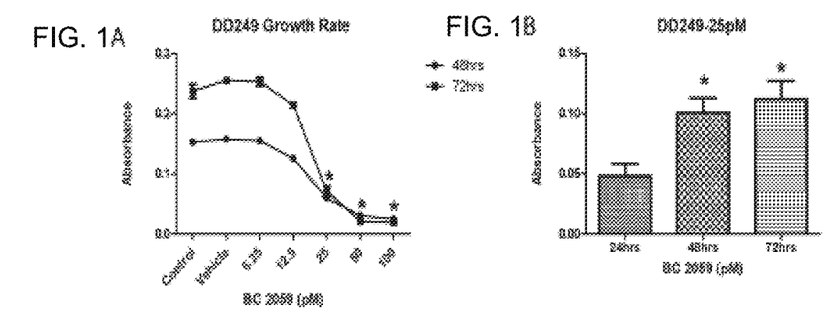
FIG. 1A shows a graph of cell growth inhibition of primary palmar fascia fibroblasts derived from the fibrotic palmar fascia cells of a patient with Dupuytren's Disease (DD) (DD249 cells) growth rate.
FIG. 1B shows a chart of cell growth inhibition of DD249 25 pM absorbance.
Figure 1C:
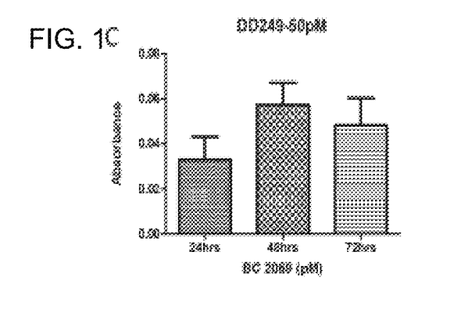
FIG. 1C shows a chart of cell growth inhibition of DD249 50 pM absorbance.

Based on the results of both proliferation/viability assays utilized and visual inspection of the cells in culture, BC-2059 was cytotoxic for both fibrosis-derived fibroblasts and syngeneic fibroblasts derived from visibly unaffected palmar fascia at concentrations >100 pM. Consistent and statistically significant differences in sensitivity to BC-2059 were evident in the proliferation/viability assays of the DD and PF cells (N=2 patients) that we assessed. As shown in FIGS. 1A through 1C, DD249 cells were viable and able to proliferate to significantly greater cell numbers in 25 pM BC-2059 over 48 and 72 hrs relative to cells treated for 24 hrs, but were unable to proliferate in 50 pM BC-2059 over 48 and 72 hrs relative to cells treated for 24 hrs.

Figures 1D, 1E:
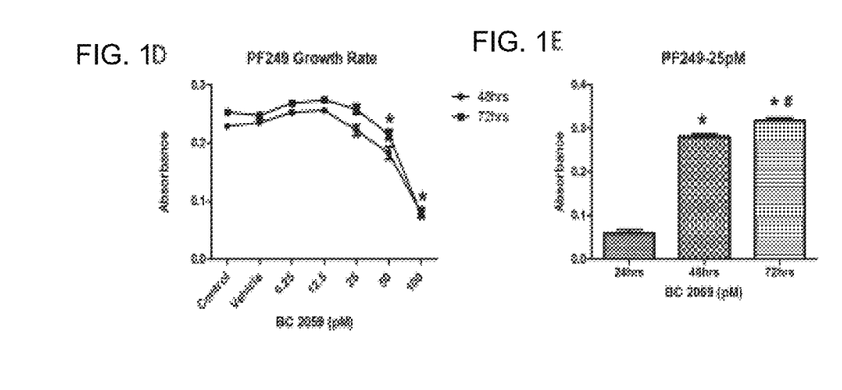
FIG. 1D shows a graph of cell growth inhibition of syngeneic primary palmar fascia fibroblasts derived from visibly non-fibrotic Palmar Fascia (PF) from the patients with Dupuytren's disease (PF249 cells) growth rate.
FIG. 1E shows a chart of cell growth inhibition of PF249 25 pM absorbance.
Figure 1F:
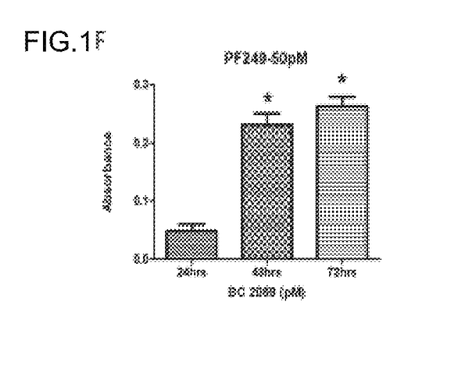
FIG. 1F shows a chart of cell growth inhibition of PF249 50 pM absorbance.

In contrast, syngeneic PF249 cells proliferated to significantly greater cell numbers in both 25 pM and 50 pM BC-2059 over 48 and 72 hrs relative to cells treated for 24 hrs. See, FIGS. 1D through 1F.

Figure 2A:
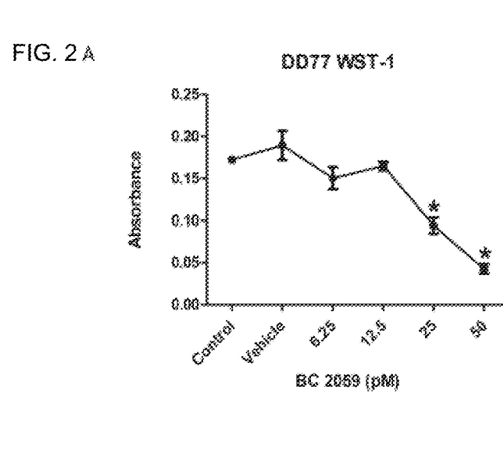
FIG. 2A shows cell growth inhibition of primary palmar fascia fibroblasts derived from the fibrotic palmar fascia cells of a patient with Dupuytren's Disease (DD) (DD77cells).
Figure 2B:
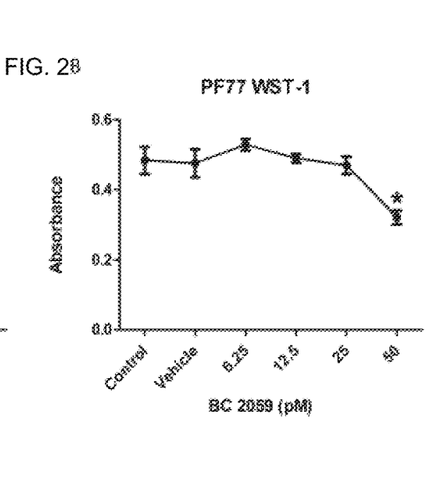
FIG. 2B shows cell growth inhibition of syngeneic primary palmar fascia fibroblasts derived from visibly non-fibrotic Palmar Fascia (PF) from a patient with Dupuytren's disease (PF77 cells).

These findings were replicated using a different assay, WST-1, in cells derived from a different patient, DD77 and PF 77, over 24 hrs, as shown in FIGS. 2A and 2B.

No discernible effects on the expression of genes that associate with nuclear β-catenin in ChIP-seq analyses of DD cells were identified in cells treated with ≥25_pM BC-2059.

Conclusion

Our preliminary analyses have identified a therapeutic window for concentrations of BC-2059 at approximately 50 pM, where the proliferation of fibrosis-derived cells, but not syngeneic palmar fascia derived cells, is inhibited. We did not identify any consistent effects on cell proliferation/viability, gene expression or contractility at ≤25 pM BC-2059 in any of our analyses, providing further confirmation of a therapeutic window above 25 pM BC-2059.

Figure 3A:
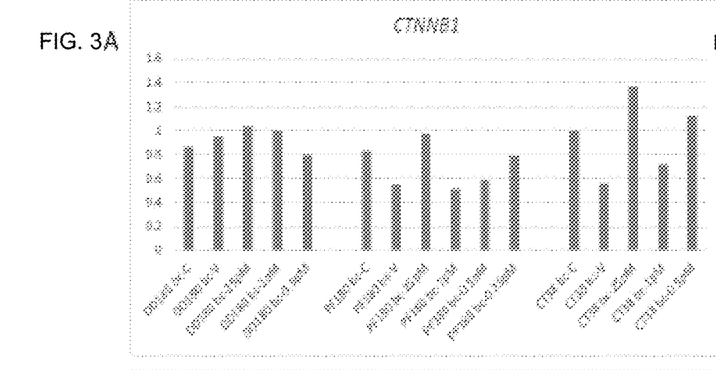
FIG. 3A shows gene expression analysis of CTNNB1 gene expression in syngeneic DD cells cultured from the explant tissues from one patient with Dupuytren's disease (DD180 cells); syngeneic PF cells cultured from the explant tissues from this patient with Dupuytren's disease (PF180 cells); and syngeneic DD cells cultured from the explant tissues from one patient with no history of Dupuytren's disease (CT38 cells).
Figure 3B:
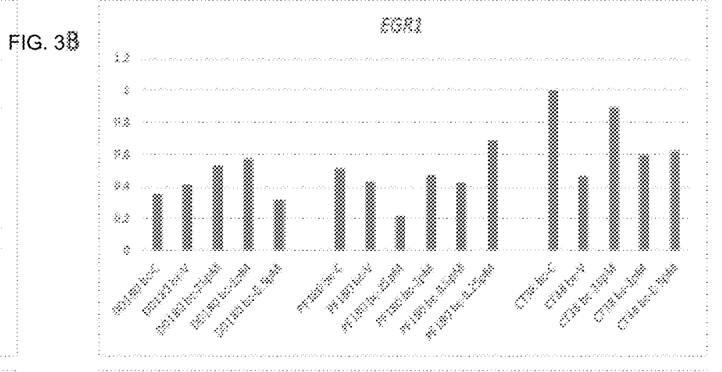
FIG. 3B shows gene expression analysis of EGR1 gene expression in DD180, PF180 and CT38 cells.
Figure 3C:
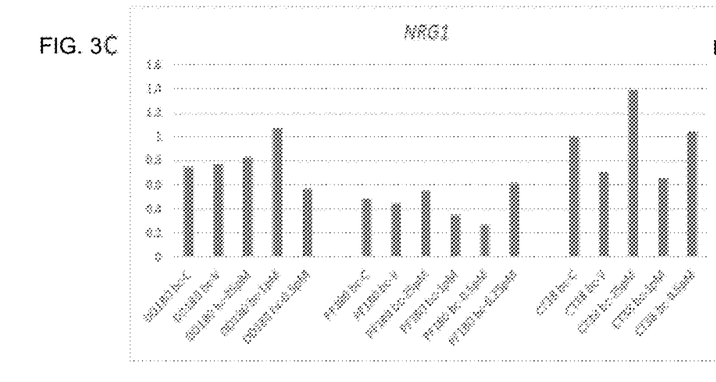
FIG. 3C shows gene expression analysis of NRG1 gene expression in DD180, PF180 and CT38 cells.
Figure 3D:
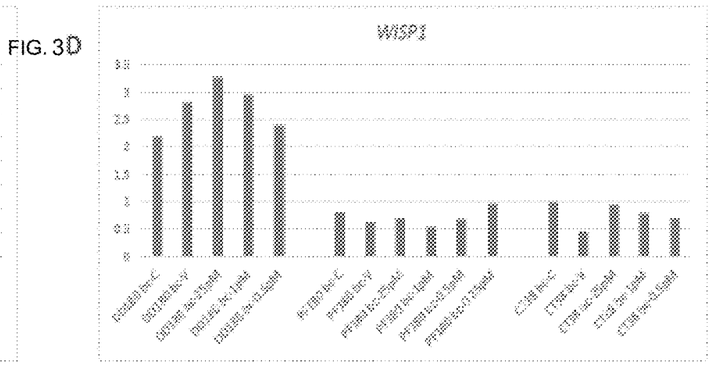
FIG. 3D shows gene expression analysis of WISP1 gene expression in DD180, PF180 and CT38 cells.
Figure 4A:
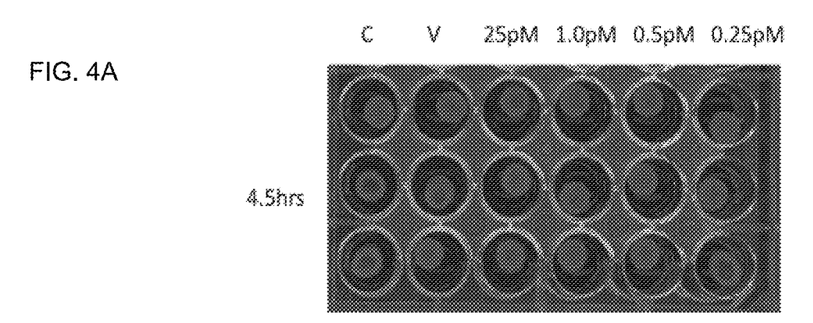
FIG. 4A shows Fibroblast-populated collagen lattice (FPCL) contraction assays of DD180 cells at 4.5 hours after lattice release.
Figure 4B:
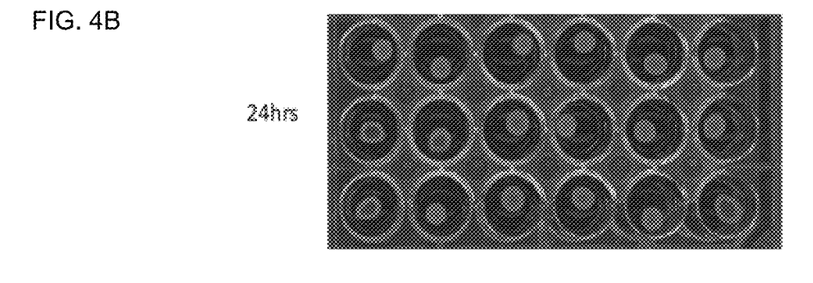
FIG. 4B shows FPCL contraction assays of DD180 cells at 24 hours after lattice release.

BC-2059 inhibits nuclear localization of beta-catenin, and not its transcription, however it was worthwhile to determine if there was any evidence of a compensatory increase in CTNNB1 mRNA levels in BC-2059 treated cells. As FIG. 3A shows, no evidence of a compensatory increase in CTNNB1 expression was detected in cells treated with ≤25_pM BC-2059. Our previous data indicate that beta-catenin associates with transcription factors in the promoters of EGR1 and NRG1 in CT cells, but not DD or PF cells, and that β-catenin associates with transcription factors in the WISP1 promoter in DD cells, but not PF or CT cells. While EGR1 and NRG1 expression levels were highest in CT cells, and WISP1 expression was highest in DD cells as expected, we did not see any evidence of BC-2059-induced changes in EGR1, NRG1 or WISP1 expression levels in cells treated with ≤25_pM BC-2059. See, FIGS. 3B-3D.

To compensate for the genetic variability between cells derived from different patients, we recommend that additional, more detailed in vitro analyses of BC-2059 be performed in the 25-100 pM range on cells derived from the fibrotic and visibly non-fibrotic palmar fascia (i.e. DD and PF cells) of at least 6 additional individuals. We have calculated that 6 patients/group (DD and PF) is sufficient to detect significance at $p<0.05$ with a power of 80%.

Example 2

Method of Treating Pulmonary Fibrosis with Tegavivint

In a pilot study, Tegavivint at 50 mg/kg was administered biw (twice a week) via tail-vein injection to C57BL/6 wild-type mice. Bleomycin was administered to the mice intratracheally on day 0 to induce pulmonary fibrosis, and Tegavivint or the vehicle (5% dextrose in water) was administered on days 6, 10, 14, 18 and 21.

The purpose of this experiment was to evaluate the effect of systemically-administered Tegavivint on bleomycin-induced pulmonary fibrosis in vivo.

Figure 5A:
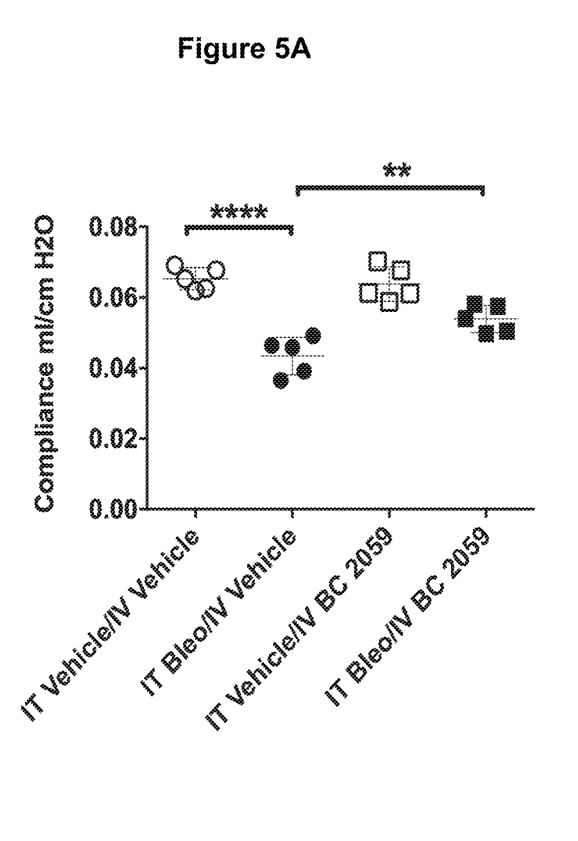
FIG. 5A shows pulmonary compliance analysis in bleomycin-induced pulmonary fibrosis mouse model with or without intravenous Tegavivint treatment.

FIG. 5A demonstrates the effect on pulmonary compliance, which is a functional measure of the lung's ability to stretch and expand. Pulmonary fibrosis is usually associated with decreased compliance, i.e. a stiff lung. As shown in FIG. 5A, animals treated with bleomycin only (second group) showed significantly decreased compliance compared with animals treated with vehicle only (first group), indicating induction of pulmonary fibrosis after bleomycin treatment; Tegavivint alone (third group) had no effect on compliance; and Tegavivint treatment after bleomycin (fourth group) partially restored the compliance measurements. Asterisks denote statistical significance at  $p<0.01$ and * $p<0.001$.

Figure 5B:
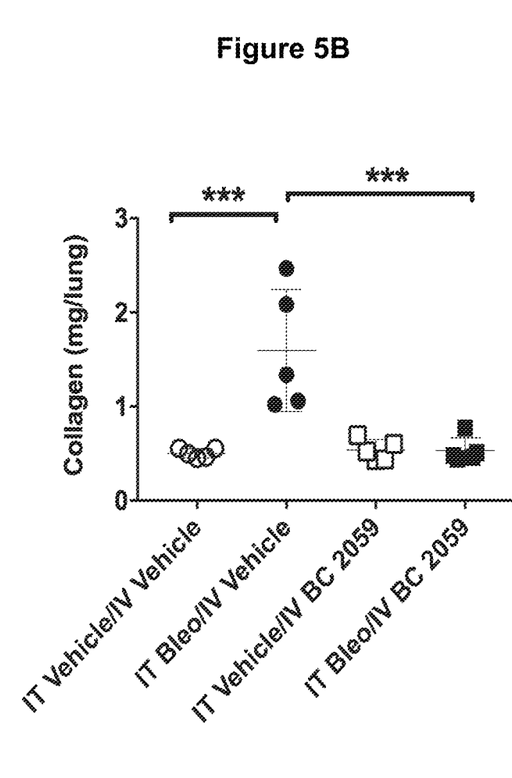
FIG. 5B shows Sircol collagen assay results in bleomycin-induced pulmonary fibrosis mouse model with or without intravenous Tegavivint treatment.

FIG. 5B demonstrate the effect on total soluble collagen content in lung tissue using the Sircol assay, which is a quantitative measure of pulmonary fibrosis, as the induction of fibrosis is associated increased new collagen synthesis and elevated soluble collagen concentration. As shown in FIG. 5B, animals treated with bleomycin only (second group) showed significantly increased soluble collagen concentration compared with animals treated with vehicle only (first group), indicating induction of pulmonary fibrosis after bleomycin treatment; Tegavivint alone (third group) had no effect; and Tegavivint treatment after bleomycin (fourth group) completely restored the collagen level to the same as vehicle-only controls. Asterisks denote statistical significance at *** $p<0.005$.

This experiment has demonstrated that Tegavivint treatment effectively attenuated bleomycin-induced pulmonary fibrosis in vivo via systemic administration.

In another pilot study, Tegavivint at 5 mg/kg was administered biw (twice a week) via intranasal delivery to C57BL/6 wild-type mice. Bleomycin was administered to the mice intratracheally on day 0 to induce pulmonary fibrosis, and Tegavivint or the vehicle (5% dextrose in water) was administered on days 6, 10, 14, 18 and 21.

The purpose of this experiment was to evaluate the effect of topically-administered Tegavivint on bleomycin-induced pulmonary fibrosis in vivo.

Figure 6:
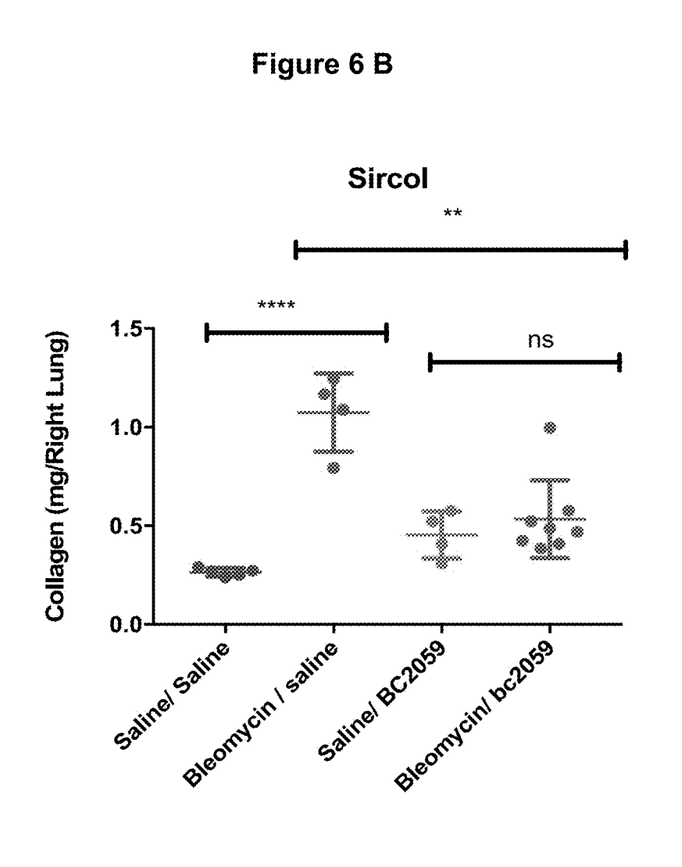
FIG. 6A shows pulmonary compliance analysis in bleomycin-induced pulmonary fibrosis mouse model with or without intranasal Tegavivint treatment.
FIG. 6B shows Sircol collagen assay results in bleomycin-induced pulmonary fibrosis mouse model with or without intranasal Tegavivint treatment.

FIG. 6A demonstrates the effect of topical Tegavivint on pulmonary compliance in the bleomycin model. As shown in FIG. 6A, animals treated with bleomycin only (second group) showed significantly decreased pulmonary compliance compared with animals treated with vehicle only (first group), indicating induction of pulmonary fibrosis after bleomycin treatment; Topical Tegavivint alone (third group) caused an increase in compliance; and Tegavivint treatment after bleomycin (fourth group) showed a trend towards increased compliance compared to the bleomycin only (second) group, although more animals may be needed to demonstrate statistical significance. Asterisks denote statistical significance at * $p<0.05$ and ** $p<0.01$.

FIG. 6B demonstrates the effect of topical Tegavivint on soluble collagen content in the bleomycin model. As shown in FIG. 6B, animals treated with bleomycin only (second group) showed significantly increased soluble collagen concentration compared with animals treated with vehicle only (first group), indicating induction of pulmonary fibrosis after bleomycin treatment; Topical Tegavivint alone (third group) showed a slight increase in collagen, which could be due to a mild inflammatory response of the lung tissue to the topical drug; and Tegavivint treatment after bleomycin (fourth group) significantly decreased the collagen level compared with the bleomycin-only (second) group. Asterisks denote statistical significance at  $p<0.01$, ** $p<0.0001$.

This experiment has demonstrated that topically-administered Tegavivint also effectively attenuated bleomycin-induced pulmonary fibrosis in vivo.

Example 3 nebulizing Delivery of Tegavivint Formulations

Tegavivint particles suspended in Poloxamer 188/sorbitol at a concentration of 25 mg/mL were used. These formulations were applied to the mice in the form of aerosols, through the method of whole body exposure. The mice were placed inside a plastic box. This box was sealed and connected by one of its sides to the outlet of the nebulizer device, and on the other side to a system of closed water. The whole procedure was carried out inside the fume hood of the animal room.

For the first experiment, the nebulizer kit of SATER LABS was used. This device uses the jet system. The device was primed with 5 ml of the drug, i.e. 125 mg of tegavivint (BC2059), for each group of 5 mice, and then the device was connected to the power source for nebulization. The energy was supplied by a DeVilbiss compressor model 646, which allows 5-7 pounds of pressure, and a flow of 6-8 liters per minute. For the second experiment, the device used was the Altera, ultrasonic nebulizer.

For the two experiments, 10 male bcat-Ex3 mice were used for each set. These mice were separated into 2 groups of 5 mice each. The first group received the drug daily, for 5 consecutive days. The second group received the drug only once (the fifth day). On day 5 all mice were sacrificed, lung harvested, and samples were stored at −30 degrees, in two labeled nylon bags, each containing the 5 samples from each group.

Results:

| Label | Group ID | Animal ID | Matrix/Bleed time | Analyte | Lung Concentration (ng/mL) | Lung Concentration (ng/g) |
| --- | --- | --- | --- | --- | --- | --- |
| Aerosol 1Day #1-1 Oct. 10, 2017 | 2 | 1 | Mouse lung | BC2059 | 14200 | 56800 |
| Aerosol 1Day #2-2 Oct. 10, 2017 | 2 | 2 | Mouse lung | BC2059 | 1300 | 5200 |
| Aerosol 1Day #3-3 Oct. 10, 2017 | 2 | 3 | Mouse lung | BC2059 | 4270 | 17100 |
| Aerosol 1Day #4-4 Oct. 10, 2017 | 2 | 4 | Mouse lung | BC2059 | 1260 | 5040 |
| Aerosol 1Day #5-5 Oct. 10, 2017 | 2 | 5 | Mouse lung | BC2059 | 4190 | 16800 |
| Aerosol 5Day #1-6 Oct. 10, 2017 | 3 | 6 | Mouse lung | BC2059 | 4640 | 18600 |
| Aerosol 5Day #2-7 Oct. 10, 2017 | 3 | 7 | Mouse lung | BC2059 | 1650 | 6600 |
| Aerosol 5Day #3-8 Oct. 10, 2017 | 3 | 8 | Mouse lung | BC2059 | 3620 | 14500 |
| Aerosol 5Day #4-9 Oct. 10, 2017 | 3 | 9 | Mouse lung | BC2059 | 3080 | 12300 |
| Aerosol 5Day #5-10 Oct. 10, 2017 | 3 | 10 | Mouse lung | BC2059 | 3550 | 14200 |
| Nebulizer 1Day #1-11 Oct. 10, 2017 | 4 | 11 | Mouse lung | BC2059 | 2840 | 11400 |
| Nebulizer 1Day #2-12 Oct. 10, 2017 | 4 | 12 | Mouse lung | BC2059 | 2910 | 11600 |
| Nebulizer 1Day #3-13 Oct. 10, 2017 | 4 | 13 | Mouse lung | BC2059 | 8660 | 34600 |
| Nebulizer 1Day #4-14 Oct. 10, 2017 | 4 | 14 | Mouse lung | BC2059 | 3780 | 15100 |
| Nebulizer 1Day #5-15 Oct. 10, 2017 | 4 | 15 | Mouse lung | BC2059 | 601 | 2400 |
| Nebulizer 5Day #1-16 Oct. 10, 2017 | 5 | 16 | Mouse lung | BC2059 | 4770 | 19100 |
| Nebulizer 5Day #2-17 Oct. 10, 2017 | 5 | 17 | Mouse lung | BC2059 | 4290 | 17200 |
| Nebulizer 5Day #3-18 Oct. 10, 2017 | 5 | 18 | Mouse lung | BC2059 | 4690 | 18800 |

-continued

| Label | Group ID | Animal ID | Matrix/Bleed time | Analyte | Lung Concentration (ng/mL) | Lung Concentration (ng/g) |
|---|---|---|---|---|---|---|
| Nebulizer 5Day #4-19 Oct. 10, 2017 | 5 | 19 | Mouse lung | BC2059 | 3040 | 12200 |
| Nebulizer 5Day #5-20 Oct. 10, 2017 | 5 | 20 | Mouse lung | BC2059 | 5730 | 22900 |
| | | | LLOQ: 20.0 ng/g | | | |

"Aerosol" refers to standard aerosol jet nebulizer (Sater Labs);
"Nebulizer" refers to nebulizer ultrasonic eRapid machine (Altera)
"1 day" refers to single-dose on Day 5;
"5 day" refers to 5 daily doses on Days 1-5.

Example 4

Efficacy of Nebulized Tegavivint in a Mouse Model of Idiopathic Pulmonary Fibrosis The purpose of this experiment was to investigate tegavivint nanosuspension in a mouse model of bleomycin-induced idiopathic pulmonary fibrosis (IPF). Test articles were as follows:

Tegavivint (BC2059) in a nano-milled suspension 25 mg/mL in 0.625% poloxamer 188 and 10% sorbitol. The compound was refrigerated at about 4° C.

Nebulizing equipment was Altera ultrasonic eRapid machine nebulizer (model #678G1002).

Animals were 8-12 week old C57BL/6 male mice (Jackson Lab, Bar Harbor, Me.).

Experimental Procedure

| Group | # of mice | Day 0 | Day 5-21 |
|---|---|---|---|
| 1 | 4 | IT PBS 50 µl | 5 ml of Vehicle (0.625% poloxamer 188/10% sorbitol) aerosol, BID |
| 2 | 4 | IT Bleomycin 0.025U in 50 µl saline | 5 ml of Vehicle (0.625% poloxamer 188/10% sorbitol) aerosol, BID |
| 3 | 5 | IT Bleomycin 0.025U in 50 µl saline | 5 ml of 25 mg/ml tegavivint aerosol, BID |

Murine model of pulmonary fibrosis was induced by intratracheally (IT) injected bleomycin (APP Pharmaceuticals, Schaumburg, Ill.). One dose of 0.025 U bleomycin dissolved in 50 microliters of Saline 0.9%, or PBS as control was administered to each animal on day 0.

Tegavivint nanosuspension was applied to Group 3 in the form of aerosols, through the method of whole body exposure. The mice were placed inside a plastic box. This box was sealed and connected by one of its sides to the outlet of the nebulizer device, and on the other side to a system of closed water. The whole procedure was carried out inside the fume hood of the animal room. In each treatment session, 5 ml of 25 mg/ml Tegavivint (125 mg) was nebulized over 15 min to each group of 4-5 mice in the chamber. To increase exposure of the mice to the aerosol, Tegavivint that precipitated in the aerosol chamber was collected with a syringe and re-nebulized a second and a third time. Mice were nebulized twice a day between day 5 and day 21 after administration of bleomycin. Group 1 and 2 received nebulized vehicle 5 ml in the same manner.

The body weight of animals was recorded on Days 0, 5, 8, 12, 16, 19, and 21.

Measurements of lung mechanics were performed on Day 21 as previously described (Morales-Nebreda L, et al. AJRCMB 2015) on Day 21 using a FlexiVent mouse ventilator (Scireq, Montreal, PQ, Canada) according to the protocols established by Scireq. A standard ventilation history for each mouse was obtained with three total lung capacity maneuvers before the forced oscillation and quasistatic pressure-volume curve protocols that were used to calculate airway resistance, dynamic and quasistatic tissue compliance, and elastance.

On Day 21 all animals were sacrificed and lungs were harvested. Total lung collagen content was evaluated using the Hydroxyproline Assay as previously described (Morales-Nebreda L, et al. AJRCMB 2015). In brief, mouse lungs were harvested and suspended in 1 ml of 0.5 M acetic acid and then homogenized, first with a tissue homogenizer (60 s on ice) and then using 15 strokes in a Dounce homogenizer (on ice). The resulting homogenate was spun (12,000×g) for 10 minutes, and the supernatant was used for subsequent analyses. Collagen standards were prepared in 0.5 M acetic acid using rat tail collagen (Sigma-Aldrich, St. Louis, Mo.). Picrosirius red dye was prepared by mixing 0.2 g of Sirius red F3B (Sigma-Aldrich) with 200 ml of water; 1 ml of the Picrosirius red dye was added to 100 µl of the collagen standard or the lung homogenates and then mixed continuously at room temperature on an orbital shaker for 30 minutes. The precipitated collagen was then pelleted and washed once with 0.5 M acetic acid (12,000×g for 15 min each). The resulting pellet was resuspended in 1 ml of 0.5 M NaOH and Sirius red staining was quantified spectrophotometrically (540 nm) using a colorimetric plate reader (Bio-Rad, Hercules, Calif.).

Results

Group 2 showed statistically significant body weight reduction after bleomycin treatment, which is one of the indicators of IPF induction. In contrast, inhaled tegavivint treatment in Group 3 reversed the body weight loss caused by the bleomycin induced lung injury.

| | Change in body weight (%) | | |
|---|---|---|---|
| Animal # | Group 1 | Group 2 | Group 3 |
| 1 | 3.24 | −10.85 | −2.83 |
| 2 | 9.13 | −1.25 | 5.2 |
| 3 | 9.85 | −4.67 | 7.3 |
| 4 | 12 | −2.62 | 7.3 |
| 5 | | | 7.9 |

Further, bleomycin induced decreased lung compliance in Group 2, which indicates the induction of fibrosis. Inhaled tegavivint treatment after bleomycin injury in Group 3 reversed the compliance values to near those of the sham-treated controls in Group 1.

|          | Compliance (ml/cm H₂0) | | |
|----------|---------|---------|---------|
| Animal # | Group 1 | Group 2 | Group 3 |
| 1 | 0.076337 | 0.044172 | 0.055153 |
| 2 | 0.068275 | 0.042324 | 0.056036 |
| 3 | 0.058057 | 0.048667 | 0.067618 |
| 4 | 0.07324  | 0.042422 | 0.054295 |
| 5 |          |          | 0.056101 |

Further, the total lung collagen content as measured by the Hydroxyproline assay showed marked increase in Group 2, indicating active fibrosis after bleomycin injury; in contrast, inhaled tegavivint treatment after bleomycin injury in Group 3 reversed this change and the collagen levels are closed to sham-treated controls in Group 1.

|          | Hydroxyproline (μg/half lung) | | |
|----------|---------|---------|---------|
| Animal # | Group 1 | Group 2 | Group 3 |
| 1 | 51.296 | 75.632 | 70.016 |
| 2 | 36.32  | 85.824 | 39.44  |
| 3 | 44.432 | 68.768 | 45.68  |
| 4 | 37.568 | 77.504 | 58.784 |
| 5 |        |        | 64.296 |

What is claimed is:

1. A method of treating pulmonary fibrosis in a patient in need thereof, comprising administering to the patient a therapeutically effective amount of a compound of formula:

or a pharmaceutically acceptable salt thereof, wherein said method prevents beta-catenin from association with trans-ducin-beta-like 1 (TBL1) protein in the patient, wherein the therapeutically effective dose is from about 0.0001 to about 1000 mg/kg/day.

2. The method of claim 1, wherein said administering is done through one or more of intravenous, parenteral, oral, inhalation (including aerosolized delivery), buccal, intranasal, rectal, intra-lesional intraperitoneal, intradermal, transdermal, subcutaneous, intra-arterial, intracardiac, intraventricular, intracranial, intratracheal, intrathecal administration, intramuscular injection, intravitreous injection, and topical application methods.

3. The method of claim 1 wherein said administering is done through aerosolized delivery.

4. The method of claim 1 wherein said administering is done through intratracheal delivery.

5. The method of claim 3, wherein said compound is formulated in a solution comprising a poloxamer and sorbitol.

6. The method of claim 3, wherein said compound is formulated in a nano-milled suspension.

* * * * *